(12) United States Patent
Juhue et al.

(10) Patent No.: US 7,276,618 B2
(45) Date of Patent: Oct. 2, 2007

(54) SURFACE TREATMENT COMPOSITION AND PROCESS

(75) Inventors: Didier Juhue, Chaponost (FR);
Marie-Jose Lina, Lyons (FR);
Anne-Claire Gayon, Paris (FR);
Jean-Marc Corpart, Sannois (FR)

(73) Assignee: E. I. du Pont de Nemours and Company, Wilmington, DE (US)

( * ) Notice: Subject to any disclaimer, the term of this patent is extended or adjusted under 35 U.S.C. 154(b) by 601 days.

(21) Appl. No.: 10/477,986

(22) PCT Filed: Jun. 21, 2002

(86) PCT No.: PCT/FR02/02167

§ 371 (c)(1),
(2), (4) Date: Nov. 12, 2003

(87) PCT Pub. No.: WO03/002572

PCT Pub. Date: Jan. 9, 2003

(65) Prior Publication Data

US 2004/0176600 A1    Sep. 9, 2004

(30) Foreign Application Priority Data

Jun. 27, 2001   (FR) .................. 01 08460

(51) Int. Cl.
   *C07F 7/04*     (2006.01)
   *C11D 3/00*     (2006.01)
(52) U.S. Cl. ............ 556/465; 556/482; 510/105; 510/109; 510/163; 510/180
(58) Field of Classification Search .......... 556/465, 556/482; 510/109, 163, 180, 105
   See application file for complete search history.

(56) References Cited

U.S. PATENT DOCUMENTS

| 3,012,006 | A | 12/1961 | Holbrook et al. |
| 3,422,131 | A | 1/1969 | Pittman et al. |
| 3,442,664 | A | 5/1969 | Heine |
| 3,450,738 | A | 6/1969 | Blochl |
| 4,024,306 | A | 5/1977 | Takamizawa et al. |
| 4,089,882 | A | 5/1978 | Takamizawa et al. |
| 4,525,425 | A | 6/1985 | Church |
| 4,549,003 | A | 10/1985 | Lim et al. |
| 4,648,904 | A | 3/1987 | DePasquale et al. |
| 4,687,707 | A | 8/1987 | Matsuo et al. |
| 4,689,181 | A | 8/1987 | Blatch |
| 4,877,654 | A | 10/1989 | Wilson |
| 4,983,459 | A | 1/1991 | Franz et al. |
| 4,990,377 | A | 2/1991 | Wilson |
| 5,011,963 | A | 4/1991 | Ogawa et al. |
| 5,051,129 | A | 9/1991 | Cuthbert et al. |
| 5,059,649 | A | 10/1991 | Maxson et al. |
| 5,124,467 | A | 6/1992 | Rodgers et al. |
| 5,274,159 | A | 12/1993 | Pellerite et al. |
| 5,962,188 | A | 10/1999 | DeBoer et al. |

FOREIGN PATENT DOCUMENTS

| JP | 11-002703 A | * | 1/1999 |
| JP | 11002703 | | 1/1999 |
| JP | 2000-327997 A | * | 11/2000 |
| JP | 2000-328230 A | * | 11/2000 |
| JP | 2000327997 | | 11/2000 |
| JP | 2000328230 | | 11/2000 |
| WO | WO99/44820 | | 9/1999 |

\* cited by examiner

*Primary Examiner*—Porfirio Nazario-Gonzalez

(57) ABSTRACT

The invention relates to a composition comprising a compound of formula (I): $R_f$—B—Ro—Z and a compound of formula (II):

$$Y-(CH_2)_m-\underset{\underset{R_p}{|}}{Si}(A)_{3-p}$$

and/or their reaction product.

22 Claims, No Drawings

SURFACE TREATMENT COMPOSITION AND PROCESS

The present invention relates to the area of surface treatments. It has as an objective, a composition and process for surface treatment of substrates using said composition. The invention also has as an objective, a compound and the process for its preparation. Furthermore, the invention has as an objective, substrates which may be obtained by said surface treatment process.

In all areas such as construction, furniture, home appliances, soiling of the surfaces is deleterious, both from the hygienic and aesthetic point of view. In areas such as transportation, particularly in airplanes or cars, the accumulation of dirt can also present a significant hazard such as causing poor vision through transparent surfaces. It then is necessary to expend effort to re-establish a minimum level of cleanliness which entails costs.

Surface treatment for substrates are known which improve their properties, notably by decreasing dirt retention.

The degree of dirt retention is generally attributed to the wettability of the substrates by polar or non-polar liquids. The wettability of a substrate is characterized by the contact angle formed by a drop of liquid on the substrate. Thus a large angle, notably above 90°, indicates that the substrate is not wetted by the liquid.

Numerous hydrophobic and oleophobic treatments have been proposed over the last few years.

Thus, U.S. Pat. No. 5,523,161 discloses a glass substrate having low wettability obtained by treatment with a perfluoroalkylalkylsilane. The treatment is rendered more durable by mixing the perfluoroalkylalkylsilane with silanes capable of being hydrolyzed.

Such perfluoroalkylalkysilane films are also described in the document EP 692 463. The abrasion resistance is improved by depositing these films onto an inorganic sublayer.

Patent application WO 99/18168 describes a coating composition with improved resistance to abrasion and to UV radiation containing a mixture of alkoxysilane and halogenosilane.

Finally, EP 491 251 and EP 492 545 disclose monomolecular films from perfluoroalkylalkylsilanes which may have an ether, ester or carbonyl function between the perfluoroalkyl group and the alkyl group.

These proposed anti-soil treatments confer to the treated substrate properties of low wettability by polar and non-polar liquids, i.e. both hydrophobic and oleophobic properties. Such liquids thus form drops with a high contact angle.

It has been observed that substrates which have been subjected to such treatments can present spots and rings which are difficult to wash off. The soiling results from small soil-containing drops which dry and deposit the soil they contain.

Currently proposed systems for treating substrates based on a large liquid contact angle are thus not completely satisfactory.

There is a need for a surface treatment which overcomes the deficiencies described above.

These deficiencies have been overcome by the present invention's surface treatment which confers on the substrate improved resistance to soiling resulting from greases and oils. It has been surprisingly observed that application to a substrate of a composition comprising a silane having perfluorinated groups and polar groups yielded very satisfactory results.

In addition, a substrate so treated presented a self-cleaning character. The term "self-cleaning character" means easy cleaning of a soiled substrate, for example by a simple stream of water without additional mechanical assistance.

An objective of the invention is thus a composition comprising a compound of formula (I):

$$R_f-B-Ro-Z \quad (I)$$

in which:
 $R_f$ represents a perfluorinated alkyl radical with a straight or branched chain comprising 1 to 20 carbon atoms, preferably 6 to 16 carbon atoms;
 B represents a bivalent group which may comprise 1 to 3 atoms of oxygen, sulfur and/or nitrogen;
 Ro represents 1 to 100, preferably 5 to 20 oxyalkylene groups, preferably oxyethylene or oxypropylene groups connected to the group B via a carbon atom; and
 Z is a hydrogen atom or, when B carries a hydroxyl group, a linear or branched chain alkyl group comprising 1 to 6 carbon atoms;

and a compound of formula (II)

$$Y-(CH_2)_m-Si(A)_{3-p} \atop R_p \quad (II)$$

in which:
 m is a whole number from 0 to 10, preferably 0 to 3;
 R represents, each independently from the other, a linear or branched alkyl group comprising 1 to carbon atoms;
 p is a whole number from 0 to 2, preferably 0;
 A represents, each independently from the other, a halogen, preferably chlorine, or an alkoxy group comprising 1 to 6 carbon atoms, preferably methoxy, ethoxy, propyloxy, and/or isopropyloxy; and
 Y represents a group comprising an isocyanate; epoxy, carboxylic acid or alcohol function, Y can so represents $Si(R_p)(A)_{3-p}$ when m is different from zero, and a group A when m is equal to zero;

and/or the reaction product.

Preferably, compound (II) is chosen among the well known non-ionic fluorinated surface active agents, for example FORAFAC® 1110D from ATOFINA or ZONYL® FSN or FSO from DuPont or UNIDYNE DS 401 from Daikin. The compound for formula (I) can be a primary or secondary alcohol. The secondary alcohol can be obtained, for example, by reaction of a fluorinated epoxide with a polyglycol ether such as $CH_3O(C_2H_4O)_n-C_2H_4OH$.

The preferred compounds of formula (II) are derivatives presenting an isocyanate or epoxy function. Examples of such compounds are γ-isocyanatopropyltriethoxysilane (SILQUEST A 1310 a silane from Witco), COATOSIL 1770 from Witco or glycidyl-3-oxypropyl-triethoxysilane (GLYEO from Huls/Sivento).

Such a composition is particularly useful to treat the surface of substrates. To this end, the composition contains, in combination with an anhydrous solvent, 1 to 50%, and in particular 10 to 40% by weight the compounds of formula (I) and (II) and/or their reaction product. Appropriate anhydrous solvents are, for example, esters such as ethyl, butyl or isopropyl acetates, ketones such as acetone, methylethylketone or methylisobutylketone.

Advantageously, the composition may comprise several compounds from each category. The composition may also contain the usual additives.

According to another embodiment of the invention, this composition may be diluted by introduction of another solvent chosen among water, the alcohols and their mixtures. Such a composition may comprise 0.05 to 5%, in particular 0.1 to 2% by weight of the cited compounds.

According to a specific embodiment, the composition is in the form of an aqueous emulsion.

The invention also has as an objective a process for preparing such a composition. This comprises the step of:
(a) dissolving a compound of formula (I) and a compound of formula (II) in an appropriate anhydrous solvent.

According to a specific embodiment, alkoxysilane or halogenosilane functions and a hydrolysis agent such as water are added for the hydrolysis. The process then comprises the following additional step:
(b) addition of a solvent chosen among water, the alcohols or their mixtures.

According to a particular embodiment, the process also comprises the following additional steps:
(c) emulsification of the solution obtained in step (b), if necessary in the presence of a surface active agent or a water soluble polymer; and if necessary,
(d) separation of the anhydrous solvent.

The invention also has as an objective a compound, of formula (III)

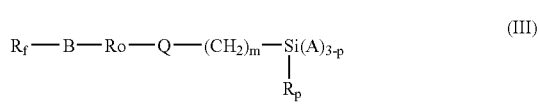

in which Rf, B, Ro, m, A and p are as defined above and Q is a carbamate, ester, alkoxysilane or ether function, preferably a carbamate or ether function.

The compound of formula (III) may be obtained notably by reaction of the alcohol function in a compound of formula (I) with the group Y in the compound of formula (II), if necessary in the presence of a catalyst.

In this embodiment of the invention, it is important to avoid hydrolysis of the alkoxysilane or halogenosilane groups, notably by operating in an anhydrous medium. Hydrolysis of these groups leads crosslinking of the silane. Appropriate conditions can easily be determined by those skilled in the art. The addition of a catalyst for the reaction may be advantageous.

The solution of the compound in the synthesis solvent constitutes a preferred embodiment of the invention. Such a composition is obtained directly after synthesis and does not require a subsequent separation.

The compound of formula (III) can be isolated in the form of a powder, a paste or a liquid, by total elimination of the synthesis solvent and incorporation into other solvents or compositions. Preferably, the compound is introduced into an appropriate anhydrous solvent such as, for example, a solvent chosen among the esters such as ethyl, butyl or isopropyl acetates, ketones such as acetone, methylethylketone or methylisobutylketone. Such a composition can be stored for extended periods of time.

According to another embodiment of the invention, the compound (III) can be synthesized in situ at the time of application of a composition according to the invention comprising its precursors.

The chemical nature of the layer formed is less well defined to the extent that crosslinking of hydrolyzed compounds (I) and (II) leads to a compound of formula (III) as well as other products. However, this embodiment leads to results of comparable quality and also presents the advantage of reducing the number of steps required in the preparation.

Another embodiment of the invention relates to a composition of the invention comprising, in addition, other solvents such as water and/or alcohols such as methanol, ethanol or isopropanol, preferably ethanol or isopropanol. Preferably, a mixture of alcohol and water is used. These compositions are notably useful as ready for use compositions.

The water added is important as a hydrolysis agent for the alkoxysilane or halogenosilane groups. The alcohols generally represent good solvents for the products contained in the composition.

These compositions can be obtained, for example, by dilution of a composition comprising and anhydrous solvent in a water-alcohol solution. The water-alcohol solution contains 0 to 100%, preferably 10 to 90% by weight of alcohol. The addition of an organic or inorganic acid such as those chosen among acetic acid or hydrochloric acid is advantageous because it catalyzes the hydrolysis of the halogenosilane or alkoxysilane functions.

The composition in an anhydrous solvent may also be diluted in water. In this case, it may be advantageous to work in the presence of one or more surface active agents and/or one or more water-soluble polymers. The solution is strongly agitated, for example using a high pressure homogenizer, then distilled to eliminate all or part of the anhydrous solvent. A stable aqueous emulsion is so obtained.

The reactions which occur when the composition is applied to a substrate are not precisely known. It appears however that the alkoxysilane or halogenosilane groups present in the composition are hydrolyzed under the effect of the hydrolysis agent into Si—OH groups, which can react together and also with Si—OH groups in the glass. The latter reaction is designated as a chemical adsorption reaction of the chemical layer deposited on the substrate. The silane groups can also react intermolecularly to form a three dimensional network comprising Si—O—Si bonds, thus conferring a high level of hardness to the deposited layer.

Another objective of the invention relates to a process for treating the surface of a substrate, comprising the step of:
(i) applying a composition of the invention to the substrate being treated in the presence of a hydrolysis agent for the alkoxysilane or halogenosilane groups present.

The substrates are preferably carefully cleaned before the surface treatment. Such a cleaning significantly improves the adhesion properties, for example by activating the hydroxyl functions on the surface of a glass substrate. In the case of glass substrates, it has been found advantageous to immerse them in a chromic acid solution followed by washing with demineralized water and drying.

The composition applied to the substrate can already contain a hydrolysis agent such as water, for example be in the form of a water-alcohol solution or an aqueous emulsion. A hydrolysis catalyst such as an organic or inorganic acid can also be added if desired.

The composition applied can also be in the form of a solution in an anhydrous solvent. In this case, the humidity in the air acts as a hydrolysis agent. The composition as described can be applied to the substrate using appropriate and known techniques, for example by spraying, brushing, coating, impregnation, immersion, at a concentration from 0.05 to 5%, preferably 0.1 to 2% active material.

A thermal treatment may be applied depending on the substrate. Thus, advantageously, but optionally, the process comprises an additional step of:

(ii) thermal treatment of the substrate after step (i) at a temperature comprised between 50 and 200° C. for a period of time comprised between 1 second and 24 hours.

Preferably, the process is carried out using water as the hydrolysis agent.

In general, the thermal treatment is shorter the higher the temperature. The primary purpose of this thermal treatment is to evaporate the solvent. Thus, it is recommended when the solvent has an elevated evaporation temperature.

It is also possible for the hydrolysis agent to be present on the substrate to which the composition is applied.

The invention further has as an objective a substrate obtained by the process described above.

Such substrates are in general inorganic or organic substrates made from transparent material, on which traces of dried drop residues are most annoying. These substrates can be subjected to another surface treatment, for example an anti-reflection treatment, before being subjected to the surface treatment of the invention. The materials involved are, for example, glass, polymethyl methacrylate and polycarbonate, and also any type of material such as stone, brick, concrete, wood, tile, leather or textiles.

The substrates treated in accordance with the process of the invention have a good resistance to oils and self-cleaning properties.

The following examples illustrate the invention without limiting it.

EXAMPLE 1

20 parts of oxyethylated fluorinated alcohol FORAFAC 1110 having the structure $C_6F_{12}C_2H_4O(CH_2-CH_2O)_nH$, where n has an average value of 11, are introduced into a 250 ml three-necked flask equipped with a temperature probe and a condenser connected to the atmosphere via a $CaCl_2$ trap. This compound was synthesized by action of ethylene oxide on the alcohol $C_6F_{13}C_2H_4OH$ using $BF_3$/ether catalysis. The dioxane produced as a by-product of the reaction was eliminated using toluene and then distilled. The oxyethylated alcohol was diluted with 42 grams of anhydrous ethyl acetate, then the catalyst was added: 0.2 parts dibutyldilaurate tin. The reaction medium was rendered inert using an anhydrous nitrogen sweep and the solution was heated under reflux at 77° C., then a stoichiometric quantity (relative to the OH group) of 3-(triethoxy)silylpropylisocyanate, of formula $(C_2H_5O)_3Si(CH_2)_3-N=C=O$, was introduced, i.e. 7.9 parts. The reaction was followed by analyzing for the $N=C=O$ using FTIR spectrometry; it is completed in 3 hours.

A solution S1 was obtained containing 40% of active material having the following structure:
$C_6F_{13}C_2H_4O(CH_2-CH_2O)_n-OC(O)NH-(CH_2)_3-Si(OC_2H_5)_3$ where n has an average value of 11.

EXAMPLE 2

This example describes the preparation of a composition for the in situ synthesis of the compound during application. 18 parts of oxyethylated fluorinated alcohol FORAFAC 1110 having the structure $C_6F_{13}C_2H_4O(CH_2-CH_2O)_nH$, where n has an average value of 11, are introduced into a 125 ml flask, dissolved in 55 parts of ethyl acetate and 18 parts of tetraethoxysilane $Si(OC_2H_5)_4$ from Aldrich are added. A solution S2 (40% dry extract) of a ready for use bi-component mixture is obtained.

EXAMPLE 3

This example describes the preparation of a composition for the in situ synthesis of the compound during application. 25 parts of oxyethylated fluorinated alcohol FORAFAC 1110 having the structure

where n has an average value of 11, are introduced into a 125 ml flask, dissolved in 55 parts of ethyl acetate and 12 parts of a silane epoxide Coatasil 1770 from WITCO having the structure:

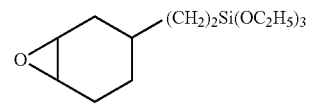

are added.

A solution S3 (40% dry extract) of a ready for use bi-component mixture is obtained.

EXAMPLE 4

This example describes the preparation of a composition for the in situ synthesis of the compound during application. 25 parts of oxyethylated fluorinated alcohol FORAFAC 1110 having the structure

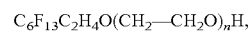

where n has an average value of 11, are introduced into a 125 ml flask, dissolved in 55 parts of ethyl acetate and 11.7 parts of a silane epoxide GLYEO from HULS/SIVENTO having the structure:

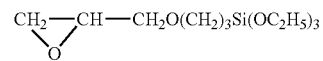

are added.

A solution S4 (40% dry extract) of a ready for use bi-component mixture is obtained.

EXAMPLE 5

20 parts of an addition product from perfluoroalkyl and hydroxylated ethylene oxide, UNIDYNE DS 401 from DAIKIN of formula $(CF_3)_2CF(CF_2)_nCH_2CHOHCH_2O(C_2H_4)_{n'}CH_3$ with n=6/8/10 and n'≈8 and 50 parts of ethyl acetate are introduced into a 100 ml three-necked flask equipped with a temperature probe, a condenser and a drop funnel. The reaction medium was rendered inert using an anhydrous nitrogen sweep and the solution was heated under reflux at 77° C., then traces of water from the surface active agent were eliminated by azeotropic distillation 0.2 parts dibutyldilaurate tin were added, then a stoichiometric quantity (relative to the OH group) of 3-(triethoxy)silylpropyl-isocyanate, of formula $(C_2H_5O)_3Si(CH_2)_3-N=C=O$, was introduced, i.e. 4.6 parts. The reaction was followed by analyzing for the N═C═O using FTIR spectrometry; it is completed in 2 hours.

A solution S5 was obtained containing 33% of active material having the following formula:

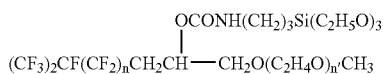

COMPARATIVE EXAMPLE 1

19.4 parts of fluorinated thiol of formula $C_8F_{17}C_2H_4SH$ and 5 parts of anhydrous ethyl acetate are introduced into a 100 ml three-necked flask equipped with a temperature probe, a condenser connected to the atmosphere via a $CaCl_2$, trap and a drop funnel.

The reaction medium was rendered inert using an anhydrous nitrogen sweep and the solution was heated under reflux at 77° C., then the drop funnel was used to introduce over 5 hours a solution containing 10 parts 2-(trimethoxy) silylpropyl methacrylate (MEMO) of formula $CH_2$═C$(CH)_3$ $C(O)O(CH_2)_3Si(OCH_3)_3$ and 0.3 parts of AIBN initiator, diluted with 40 parts of anhydrous ethyl acetate.

The solution SC1 obtained contains 39.5% of the monoaddition product of formula: $C_8F_{17}C_2H_4S$—$CH_2$—$C(CH)_3$ $C(O)O(CH_2)_3Si(OCH_3)_3$.

COMPARATIVE EXAMPLE 2

45 parts of an oxyethylated surface active agent, BRIJ 76 from ICI (of formula $CH_3(CH_2)_{17}(OC_2H_4)_{10}OH$ and 50 parts of anhydrous ethyl acetate are introduced into a 100 ml three-necked flask equipped with a temperature probe, a condenser and a drop funnel. The reaction medium was rendered inert using an anhydrous nitrogen sweep and the solution was heated under reflux at 77° C., then traces of water from the surface active agent were eliminated by azeotropic distillation. 0.1 parts dibutyldilaurate tin were added, then a stoichiometric quantity (relative to the OH group) of 3-(triethoxy)silylpropylisocyanate, of formula $(C_2H_5O)_3Si(CH_2)_3$—N═C═O, was introduced, i.e. 17.1 parts. The reaction was followed by analyzing for the N═C═O using FTIR spectrometry; it is completed in 5 hours.

A solution SC2 was obtained containing 55% of active material having the following structure: $CH_3(CH_2)_{17}$ $(OC_2H_4)_{10}OCONH$—$(CH_2)_3$—$Si(OC_2H_5)_3$ The solutions S1, S2, S3, S4, S5, SC1 and SC2 obtained in the examples were then diluted in a mixture of water/isopropanol (ratio 10/90) and adjusted to a pH 5 with acetic acid. Solutions containing 0.1% by weight active materials were obtained.

These solutions were then applied to inorganic glass plates (slides) used for optical microscopy which were previously cleaned by immersion in chromic acid solution and then washed with demineralized water and dried. The glass plates so prepared were then immersed in aqueous solutions containing 0.1% active material for 1 hour at ambient temperature, then pulled put vertically at 0.5 mm/minute using a KRUSS tensiometer, and finally dried for 1 hour at 60° C. in an oven.

The oil resistance and the washability of the glass plates treated in this manner were then evaluated.

The following tests were used to evaluate the performance of the substrates treated in accordance with the invention:

Oil Resistance (Oleophobic Character)

The oil resistance is characterized by measuring the contact angle of drops of paraffin oil, dodecane and tetradecane deposited on the treated substrate. A comparative measurement is carried out on an untreated glass plate. The angle is measured using an ERMA G1 type goniometer.

A small volume drop (≈1.5 µL) of oil is deposited on the treated substrate using a syringe controlled by a micrometer screw. The substrate is maintained horizontal on a platen whose horizontal position is controlled by a bubble level. The angle is measured at the two tangents to the points of contact of the drop on the substrate. The average of these two angles on at least four drops is calculated.

Self-cleaning or Washability Test

The self-cleaning character is determined using a variant of the so-called "spray test" described in standard AATCC 22-1989 which involves mounting a substrate according to the invention which has been soiled onto a support inclined at 45", then pouring 50 ml of water from a funnel providing with a watering pump over a period of about 5 seconds from a height of about 20 cm.

The substrates obtained by treatment with the solutions of the invention and of the comparative examples are previously soiled by spraying with paraffin oil which has been colored red using an organol type dye. The deposit is of the order of 30 g/m². Water is dropped on the sample as described above and it is visually examined. The persistance of colored oil spots is noted as well as the presence of residual water drops.

The results are given in the following table.

Comparative example 1 is an alkoxysilane carrying a perfluorinated group and also an ester and thioether group. It has a strongly oleophobic character as seen from the contact angles measured relative to the non-polar liquids. It is possible to observe the appearance of small oil droplets as soon as the substrate is sprayed with the colored oil. However, this type of treatment does not allow elimination of the soil by simple passage of water. In fact, small colored spots remain which presumably are derived from drying of small droplets containing impurities.

Comparative example 2 relates to a compound which carries hydrophilic groups but no perfluorinated groups. It is seen from the small contact angles measured that this compound is oleophilic. It is in fact observed that the substrate is wetted by paraffin oil without formation of droplets. In addition, the substrate has a hydrophilic nature. However, this property is not sufficient since it is possible to observe colored tracks after passage of water.

The test on untreated glass shows the unsatisfactory behavior of a substrate having an oleophilic and hydrophobic character.

| | θ (°) paraffin oil | θ (°) dodecane | θ (°) tetradecane | Washability | |
|---|---|---|---|---|---|
| Treatment | (° C.) | (° C.) | (° C.) | Spots | Water drops |
| S1 | 61 | 52 | 59 | − | − |
| SC1 | 82 | 73 | 79 | +++ | ++ |
| SC2 | <20 | <20 | <20 | +++ | + |
| S2 | 61 | 44 | 50 | − | − |

-continued

| Treatment | θ (°) paraffin oil (° C.) | θ (°) dodecane (° C.) | θ (°) tetradecane (° C.) | Washability Spots | Water drops |
|---|---|---|---|---|---|
| S3 | 61 | 46 | 54 | − | − |
| S4 | 61 | 52 | 56 | − | − |
| S5 | n.d. | n.d. | n.d. | − | − |
| Untreated glass | <20 | <20 | <20 | ++ | +++ |

−: practically no visible spot or drop
+: a few visible spots or drops
++: more numerous visible spots or drops
+++: very numerous visible spots or drops
n.d.: not determined In contrast, it can clearly be seen that the substrates treated with compositions of the invention yield very satisfactory results, namely the near absence of colored paraffin oil spots and also of small water droplets which may later reinforce the appearance of dirt on the substrate.

Thus, the compositions of the invention provide an effective anti-soil treatment for substrates, consisting in an elimination of dirt by simple passage of water.

The invention claimed is:

1. A composition comprising a compound of formula (I):

$$R_f\text{—}B\text{—}Ro\text{—}Z \qquad (I)$$

in which:
  $R_f$ represents a perfluorinated alkyl radical with a straight or branched chain comprising 1 to 20 carbon atoms;
  B represents a bivalent group which may comprise 1 to 3 atoms of oxygen, sulfur and/or nitrogen;
  Ro represents 1 to 100 oxyalkylene groups connected to the group B via a carbon atom; and
  Z is a hydrogen atom or, when B carries a hydroxyl group, a linear or branched chain alkyl group comprising 1 to 6 carbon atoms;
and a compound of formula (II)

$$Y\text{—}(CH_2)_m\text{—}Si(A)_{3-p} \atop R_p \qquad (II)$$

in which:
  m is a whole number from 0 to 10;
  R represents, each independently from the other, a linear or branched alkyl group comprising 1 to 6 carbon atoms;
  p is a whole number from 0 to 2;
  A represents, each independently from the other, a halogen, or an alkoxy group comprising 1 to 6 carbon atoms; and
  Y represents a group comprising an isocyanate, epoxy, carboxylic acid or alcohol function, Y can also represent $Si(R_p)(A)_{3-p}$ when m is different from zero, and a group A when m is equal to zero;
and/or their reaction product.

2. Composition according to claim 1, in which $R_f$ in formula (I) comprises 6 to 16 carbon atoms.

3. Composition according to claim 1, in which Ro in formula (I) represents 5 to 20 oxyalkylene groups.

4. Composition according to claim 1, in which m in formula (II) is a number from 0 to 3.

5. Composition according to claim 1, in which Y in formula (II) comprises an isocyanate or epoxy function.

6. Composition according to claim 1, in which A in formula (II) represents a methoxy, ethoxy, propyloxy, and/or isopropyloxy group.

7. Composition according to claim 1, in which p is 0.

8. Composition according to claim 1, comprising 1 to 50% by weight of the compounds of formula (I) and (II) and/or the reaction product thereof.

9. Composition according to claim 1, comprising in addition a solvent chosen among water, the alcohols and their mixtures.

10. Composition according to claim 1 comprising 0.05 to 5% by weight of active material.

11. Composition according to claim 1 in the form of an aqueous emulsion.

12. Process for preparing a composition according to any claim 1 comprising the step of:
  (a) dissolving a compound of formula (I) and a compound of formula (II) in an anhydrous solvent.

13. Process according to claim 12, comprising the following additional step:
  (b) addition of a solvent chosen among water, an alcohol or their mixtures.

14. Process according to claim 13, comprising the following additional steps:
  (c) emulsification of the solution obtained in step (b), if necessary in the presence of a surface active agent or a water soluble polymer; and if necessary,
  (d) separation of the anhydrous solvent.

15. Compound of formula (III)

$$R_f\text{—}B\text{—}Ro\text{—}Q\text{—}(CH_2)_m\text{—}Si(A)_{3-p} \atop R_p \qquad (III)$$

in which:
  m is a whole number from 0 to 10;
  $R_f$ represents a perfluorinated alkyl radical with a straight or branched chain comprising 1 to 20 carbon atoms;
  B represents a bivalent group which may comprise 1 to 3 atoms of oxygen, sulfur and/or nitrogen;
  Ro represents 1 to 100 oxyalkylene groups connected to the group B via a carbon atom;
  R represents, each independently from the other, a linear or branched alkyl group comprising 1 to 6 carbon atoms;
  p is a whole number from 0 to 2;
  A represents, each independently from the other, a halogen, or an alkoxy group comprising 1 to 6 carbon atoms;
  and Q is a carbamate, ester, alkoxysilane or ether function.

16. Compound according to claim 15 in which Q is a carbamate or ether function.

17. Process for preparing a compound of claim 15 or 16 by reaction of the alcohol function in a compound of formula (I) with the group Y in the compound of formula (II), optionally in the presence of catalyst wherein formula (I) is $$R_f\text{—}B\text{—}Ro\text{—}Z$$

in which:
  $R_f$ represents a perfluorinated alkyl radical with a straight or branched chain comprising 1 to 20 carbon atoms;
  B represents a bivalent group which may comprise 1 to 3 atoms of oxygen, sulfur and/or nitrogen;

Ro represents 1 to 100 oxyalkylene groups connected to the group B via a carbon atom; and Z is a hydrogen atom or, when B carries a hydroxyl group, a linear or branched chain alkyl group comprising 1 to 6 carbon atoms; and wherein formula (II) is

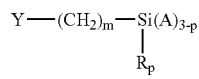

in which:

m is a whole number from 0 to 10;

R represents, each independently from the other, a linear or branched alkyl group comprising 1 to 6 carbon atoms;

p is a whole number from 0 to 2;

A represents, each independently from the other, a halogen, or an alkoxy group comprising 1 to 6 carbon atoms; and Y represents a group comprising an isocyanate, epoxy, carboxylic acid or alcohol function, Y can also represent $Si(R_p)(A)_{3-p}$ when m is different from zero, and a group A when m is equal to zero.

18. Surface treatment process comprising the step of:

i) applying a composition according to claim 1 to a substrate being treated in the presence of a hydrolysis agent for the alkoxysilane or halogenosilane groups present.

19. Process according to claim 18 which comprises an additional step of:

ii) thermal treatment of the substrate obtained in step (i) at a temperature comprised between 50 and 200° C. for a period of time comprised between 1 second and 24 hours.

20. Process according to claim 18 in which the hydrolysis agent is water.

21. Treated substrate obtained by the process according to any of the claims 18 to 20.

22. Treated substrate according to claim 21, in which the substrate is chosen among glass, polymethyl methacrylate and polycarbonate.

* * * * *